United States Patent

Malewicz

[11] Patent Number: 5,571,078
[45] Date of Patent: Nov. 5, 1996

[54] RANGE-OF-MOTION ANKLE SPLINT

[75] Inventor: Andrzej Malewicz, Minneapolis, Minn.

[73] Assignee: Empi, Inc., Minneapolis, Minn.

[21] Appl. No.: 472,339

[22] Filed: Jun. 7, 1995

Related U.S. Application Data

[63] Continuation-in-part of Ser. No. 382,993, Feb. 3, 1995, Pat. No. 5,520,627, which is a continuation-in-part of Ser. No. 205,837, Mar. 4, 1994, Pat. No. 5,437,619, which is a continuation-in-part of Ser. No. 85,758, Jun. 19, 1993, Pat. No. 5,399,154.

[51] Int. Cl.⁶ .................................................. A61F 5/00
[52] U.S. Cl. .................... 602/27; 602/5; 602/16; 602/23; 128/882
[58] Field of Search .......................... 602/23, 27, 60, 602/62, 65, 5, 16; 128/882

[56] References Cited

U.S. PATENT DOCUMENTS

| | | |
|---|---|---|
| 44,799 | 5/1864 | Shepard . |
| 1,847,823 | 1/1932 | Dresser . |
| 1,851,241 | 3/1932 | Dresser . |
| 2,395,578 | 7/1943 | Svoboda . |
| 2,413,634 | 12/1946 | Kolarik . |
| 2,646,793 | 7/1953 | Swiech et al. . |
| 2,675,578 | 4/1954 | Atwood et al. . |
| 2,797,431 | 7/1957 | Loria . |
| 2,934,785 | 5/1960 | Heuer . |
| 3,086,521 | 4/1963 | Desai et al. . |
| 4,180,870 | 1/1980 | Radulovic et al. . |
| 4,252,111 | 2/1981 | Chao et al. . |
| 4,397,308 | 8/1983 | Hepburn . |
| 4,433,679 | 2/1984 | Mauldin et al. . |
| 4,456,002 | 6/1984 | Barber et al. . |
| 4,485,808 | 12/1984 | Hepburn . |
| 4,489,718 | 12/1984 | Martin . |
| 4,493,316 | 1/1985 | Reed et al. . |
| 4,508,111 | 4/1985 | Hepburn . |
| 4,520,804 | 6/1985 | DiGeorge . |
| 4,538,600 | 9/1985 | Hepburn . |
| 4,565,190 | 1/1986 | Pirmantgen ................ 602/26 |
| 4,602,620 | 7/1986 | Marx . |
| 4,624,246 | 11/1986 | Ajemian . |
| 4,633,867 | 1/1987 | Kausek et al. . |
| 4,643,177 | 2/1987 | Sheppard et al. . |
| 4,657,000 | 4/1987 | Hepburn . |
| 4,719,906 | 1/1988 | DeProspero . |
| 4,726,361 | 2/1988 | Farley . |
| 4,729,254 | 3/1988 | Nogami . |
| 4,738,252 | 4/1988 | Friddle et al. . |
| 4,753,229 | 6/1988 | Sutherland ................ 602/65 X |
| 4,790,301 | 12/1988 | Silfverskiold . |
| 4,817,588 | 4/1989 | Bledsoe . |
| 4,844,057 | 7/1989 | Hoy . |
| 4,862,878 | 9/1989 | Davison et al. . |
| 4,865,024 | 9/1989 | Hensley et al. . |

(List continued on next page.)

FOREIGN PATENT DOCUMENTS 1426-528-A  9/1988  U.S.S.R. .................... 602/20

Primary Examiner—Richard J. Apley
Assistant Examiner—Kim M. Lee
Attorney, Agent, or Firm—Kinney & Lange, P.A.

[57] ABSTRACT

A range-of-motion splint for applying torque to an ankle joint of a patient is disclosed. The splint includes a foot plate for supporting the foot of a patient. First and second foot brackets are connected to the foot plate via first and second fastening means, respectively. First and second pivot means pivotally connect a first and a second ankle bracket to the first and second foot brackets, respectively. First and second torque applying means are connected to the first and second foot brackets and the first and second ankle brackets, respectively. The first torque applying means applies torque between the first foot bracket and the first ankle bracket, while the second torque applying means supplies torque between the second foot bracket and the second ankle bracket. Calf securing means are connected to the first and second ankle brackets for securing the first and second ankle brackets to a calf of the patient. A plurality of ankle straps are connected to the first and second pivot means for securing the first and second foot brackets and the first and second ankle brackets to an ankle of the patient.

21 Claims, 7 Drawing Sheets

U.S. PATENT DOCUMENTS

| | | | |
|---|---|---|---|
| 4,873,967 | 10/1989 | Sutherland et al. | 602/26 |
| 4,947,835 | 8/1990 | Hepburn et al. | |
| 5,000,169 | 3/1991 | Swicegood et al. | 602/26 |
| 5,002,044 | 3/1991 | Carter. | |
| 5,002,045 | 3/1991 | Spademan. | |
| 5,025,782 | 6/1991 | Salerno | 602/26 |
| 5,036,837 | 8/1991 | Mitchell et al. | 602/26 |
| 5,052,379 | 10/1991 | Airy et al. | |
| 5,060,640 | 10/1991 | Rasmusson. | |
| 5,063,917 | 11/1991 | Young et al. | 602/26 |
| 5,099,860 | 3/1992 | Amerin | 602/65 X |
| 5,167,612 | 12/1992 | Bonutti | 602/20 |
| 5,242,379 | 9/1993 | Harris et al. | 602/26 |
| 5,330,419 | 7/1994 | Toronto et al. | 602/65 X |
| 5,352,190 | 10/1994 | Fischer et al. | 602/26 |
| 5,358,469 | 10/1994 | Patchel et al. | 602/5 |

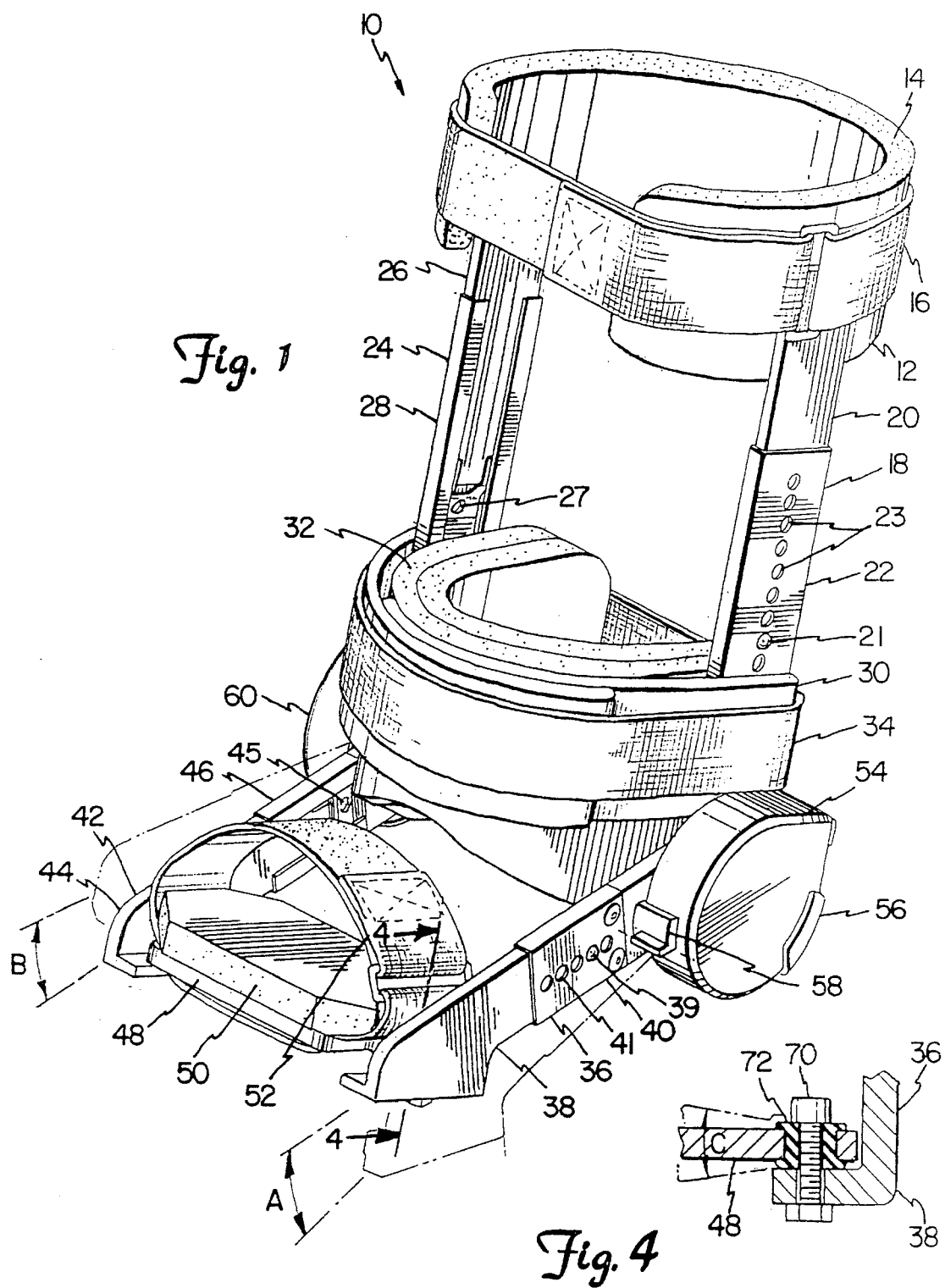

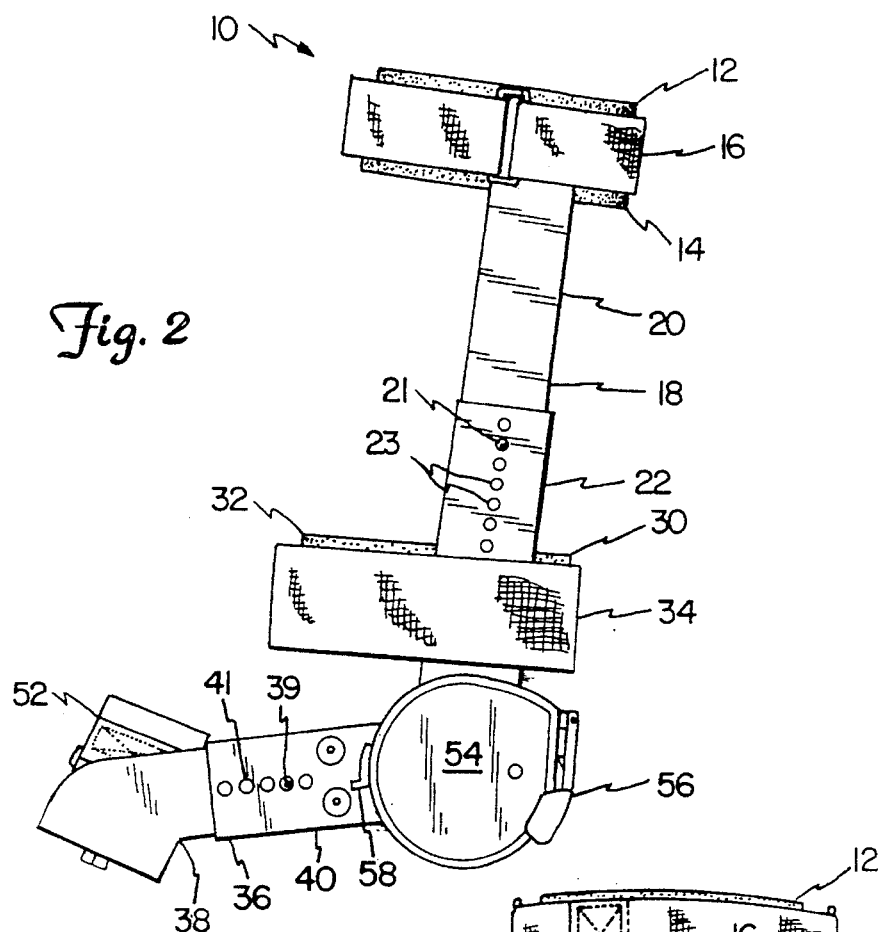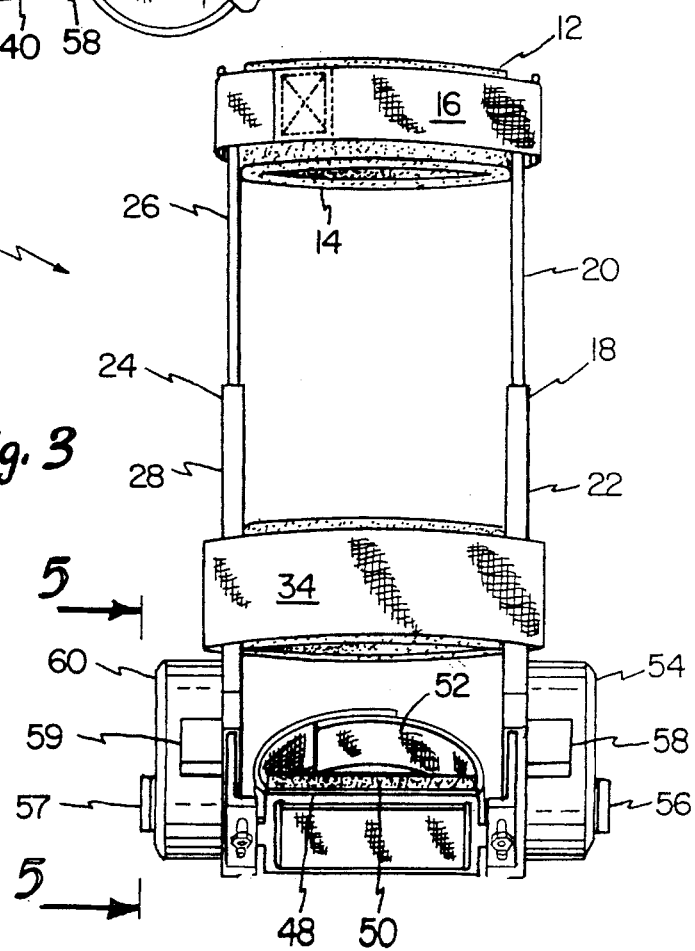

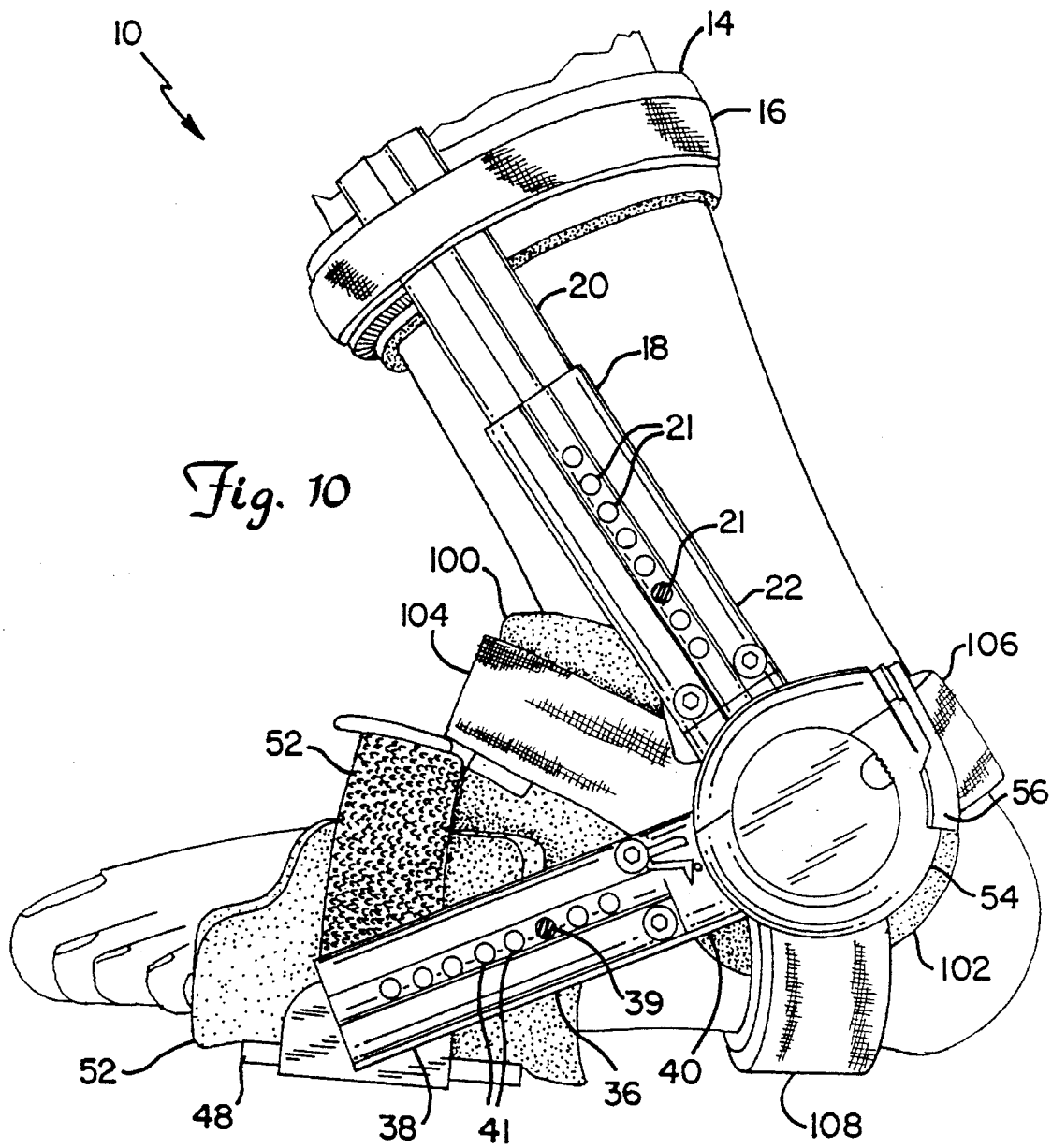

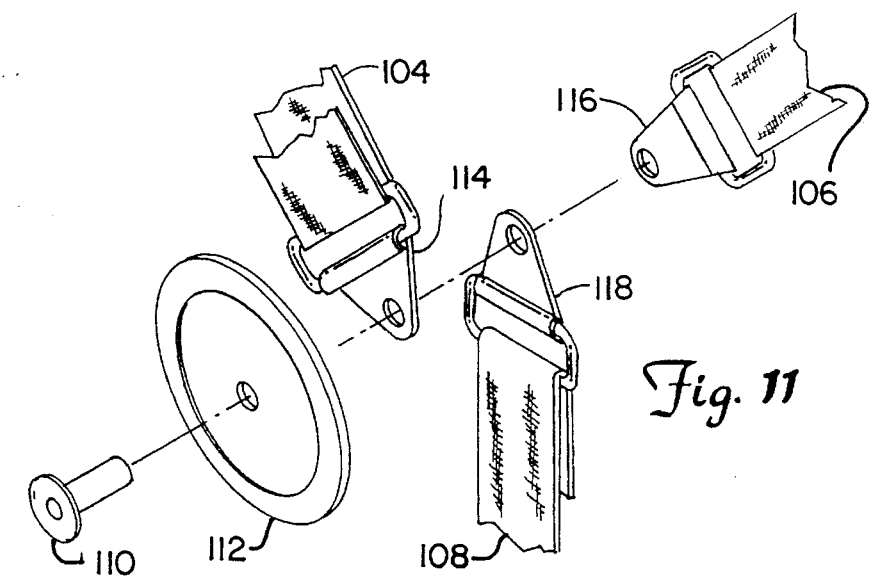
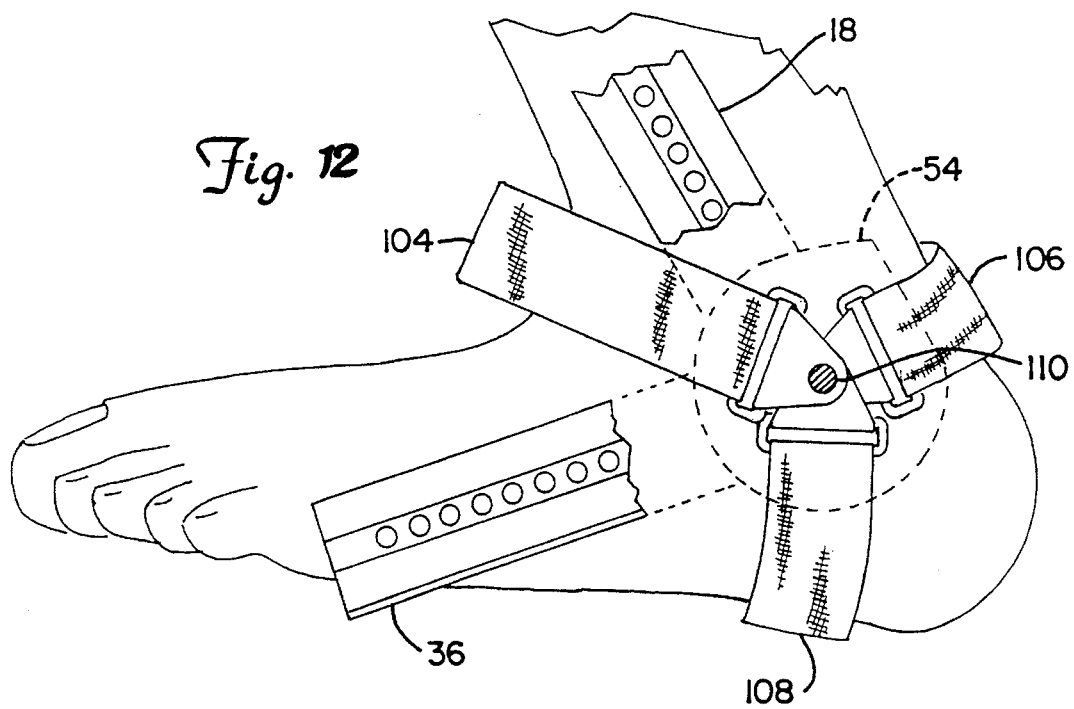

RANGE-OF-MOTION ANKLE SPLINT

REFERENCE TO RELATED APPLICATIONS

This application is a continuation-in-part of commonly assigned and co-pending U.S. patent application Ser. No. 08/382,993, U.S. Pat. No. 5,520,627, filed Feb. 3, 1995, entitled RANGE-OF-MOTION ANKLE SPLINT, which is a continuation-in-part of commonly assigned and co-pending U.S. patent application Ser. No. 08/205,837, filed Mar. 4, 1994, U.S. Pat. No. 5,437,614 entitled RANGE-OF-MOTION SPLINT WITH ECCENTRIC SPRING, which is a continuation-in-part of commonly assigned U.S. Pat. No. 5,399,154, issued Mar. 21, 1995, entitled CONSTANT TORQUE RANGE-OF-MOTION SPLINT.

Reference is made to the following commonly assigned and co-pending application: U.S. patent application Ser. No. 08/383,063, filed Feb. 3, 1995, entitled HALO HOOKS FOR RANGE-OF-MOTION SPLINT by Andrzej Malewicz.

BACKGROUND OF THE INVENTION

The present invention relates generally to splint assemblies, and more particular to dynamic splints or braces for applying torque across joints undergoing rehabilitative therapy.

Injuries or surgery to ankles, wrists, elbows, knees and other joints often results in flexion or extension contractures. These debilitating conditions prevent the patient from fully flexing (in the case of an extension contracture) or extending (in the case of a flexion contracture) the injured joint. Range-of-motion (ROM) splints are dynamic devices commonly used during physical rehabilitative therapy to increase the range of motion over which the patient can flex or extend the joint. Splints of this type are known, and disclosed, for example, in the Mitchell et al. patent entitled DYNAMIC EXTENSION SPLINT, U.S. Pat. No. 5,036,837.

Commercially available range-of-motion splints typically include spring loaded brace sections for applying torque to the injured joint in opposition to the contracture. This force tends to gradually increase the working range or angle of joint motion. Springs, however, are passive devices and exert decreasing amounts of force as they retract. Most range-of-motion splints, therefore, require continual adjustment to maintain a constant amount of applied torque as the patient's range of joint motion increases during therapy. These torque adjusting procedures are time consuming and inconvenient.

In addition, with respect to range-of-motion splints for an ankle joint, commercially available splints do not provide for flexibility between the foot bracket positioned on the side of the foot of the user and the foot plate which supports the foot of the user. This flexibility between the two components is necessary to accommodate foot inversion, which is the twisting of the foot during flexion or extension contractures. Without compensating for foot inversion, an ankle range-of-motion splint will not provide the most beneficial rehabilitative therapy as possible.

It is evident that there is a continuing need for improved range-of-motion splints for an ankle joint. In particular, there is a need for splints capable of applying relatively constant torque over the entire working joint angle range without adjustments. The amount of torque applied by the splint should also be adjustable to suit the needs of different patients. In addition, the splint should provide for flexibility between the foot bracket positioned on the side of the foot of the user and the foot plate which supports the foot of the user to accommodate for foot inversion.

SUMMARY OF THE INVENTION

The present invention is a range-of-motion splint for providing torque to an ankle joint of a patient undergoing rehabilitative therapy. The range-of-motion splint is designed so that it accommodates foot inversion, which is the twisting of the foot during flexion contractures of the ankle joint.

The range-of-motion ankle splint includes a foot plate for supporting the foot of a patient. First and second foot brackets are connected to the foot plate via first and second fastening means, respectively. A first flexible grommet is positioned about the first fastening means to flexibly separate the foot plate from the first foot bracket, while a second flexible grommet is positioned about the second fastening means to flexibly separate the foot plate from the second foot bracket. First and second pivot means pivotally connect a first and second ankle bracket to the first and second foot brackets. First and second torque applying means are connected to the first and second foot brackets and the first and second ankle brackets, respectively. The first torque applying means applies torque between the first foot bracket and the first ankle bracket, while the second torque applying means supplies torque between the second foot bracket and the second ankle bracket.

In one preferred embodiment, the range-of-motion ankle splint further includes foot securing means connected to the foot plate for securing the foot of the patient to the foot plate. The foot securing means further comprises a pad of flexible material having hook and loop material. The splint includes a plurality of ankle straps connected to the first and second pivot means for securing the first and second foof brackets and the first and second ankle brackets to an ankle of the patient. A calf hook is also provided and is connected to the first and second ankle brackets. Calf securing means secures the calf hook to a calf of a patient.

BRIEF DESCRIPTION OF THE DRAWINGS

FIG. 1 is a perspective view of a range-of-motion ankle splint.

FIG. 2 is a side view of a range-of-motion ankle splint.

FIG. 3 is a front view of range-of-motion ankle splint.

FIG. 4 is a sectional view of the fastening means which flexibly fastens the foot plate to the foot bracket as shown from line 4—4 of FIG. 1.

FIG. 10 is a side view of an alternate embodiment of a range-of-motion ankle splint.

FIG. 11 is an exploded view of a portion of the alternate embodiment shown in FIG. 10.

FIG. 12 is a second side view of the alternate embodiment of the range-of-motion ankle splint with portions of the splint removed for clarity.

DETAILED DESCRIPTION OF THE PREFERRED EMBODIMENTS

Figure 5:
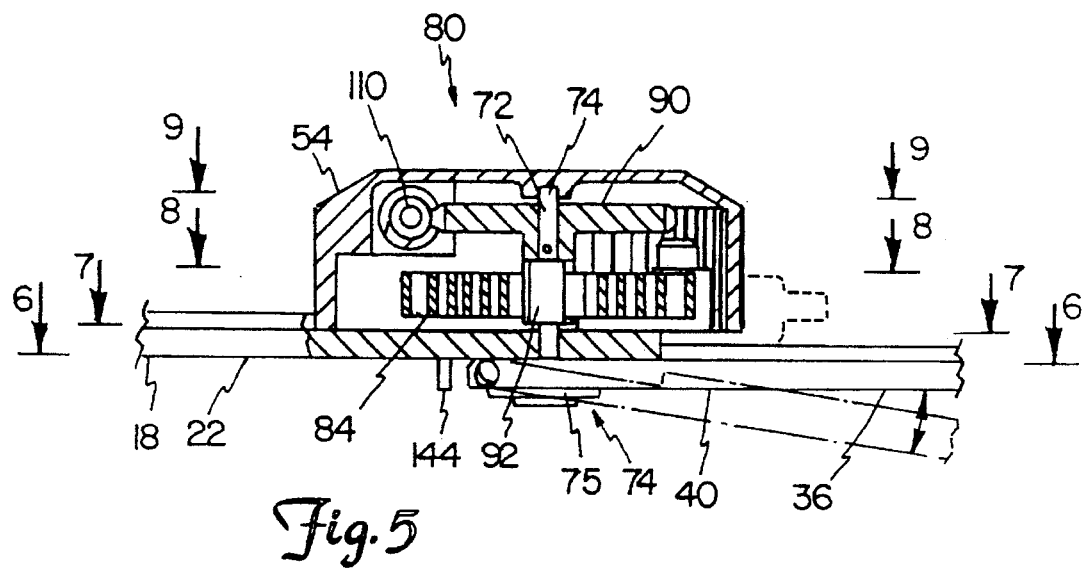
FIG. 5 is a sectional side view of the drive assembly of the present invention as shown from line 5—5 of FIG. 3.

The present invention relates to range-of-motion splint 10 shown in FIGS. 1–3 for applying torque to an ankle joint of a patient. FIG. 1 is a perspective view of range-of-motion splint 10. FIG. 2 is a side view and FIG. 3 is a front view of splint 10. Splint 10 includes calf hook 12, calf padding 14, calf strap 16, ankle bracket 18 comprising first telescoping bracket 20 having pin 21 and second telescoping bracket 22 having holes 23, ankle bracket 24 comprising first telescoping bracket 26 having pin 27 and second telescoping bracket 28, ankle hook 30, ankle padding 32, ankle strap 34, foot bracket 36 comprising first telescoping bracket 38 having pin 39 and second telescoping bracket 40 having holes 41, foot bracket 42 comprising first telescoping bracket 44 having pin 45 and second telescoping bracket 46, foot plate 48, foot padding 50, foot strap 52, housing 54, torque adjustment arms 56 and 57, locks 58 and 59, and housing 60 which houses a drive assembly, a pivot assembly, a lock mechanism and a torque adjustment mechanism.

In operation, a patient having an ankle joint which has undergone a flexion or extension contracture will place his foot through calf strap 16, ankle strap 34 and foot strap 52. Ankle brackets 18 and 24 can be adjusted via holes 23 and pins 21 and 27 such that calf hook 12 and ankle hook 30 are properly positioned on the patient. Likewise, foot brackets 36 and 42 can be adjusted via holes 41 and pins 39 and 45 such that foot plate 48 and foot strap 52 are properly positioned on the patient. Calf strap 16, ankle strap 34 and foot strap 52 can then be individually tightened. In one preferred embodiment, calf strap 16, ankle strap 34 and foot strap 52 are formed from hook and loop material such as material sold under the trademark VELCRO. Range-of-motion splint 10 will then be properly secured to the foot and lower leg of the patient. Calf padding 14, ankle padding 32 and foot padding 50 prevent irritation and bruising of the patient's lower leg and foot.

Ankle bracket 18 is connected to foot bracket 36 via a pivot pin (not shown in FIGS. 1–3). Housing 54 houses a torque adjustment mechanism (not shown in FIGS. 1–3) which is connected to both ankle bracket 18 and foot bracket 36 to provide torque between ankle bracket 18 and foot bracket 36. Likewise, ankle bracket 24 is connected to foot bracket 42 by a pivot pin (not shown in FIGS. 1–3). In addition, housing 60 houses a torque adjustment mechanism (not shown in FIGS. 1–3) which provides a torque between ankle bracket 24 and foot bracket 42. The torque adjustment means housed by housing 60 is independent of the torque adjustment means housed in housing 54. Thus, the torque applied to the left side of the foot and ankle joint of a patient is independent of the torque applied to the right side of the foot and ankle joint of the patient.

FIG. 4 is a sectional view of a portion of range-of-motion splint 10 as seen from line 4—4 shown in FIG. 1. As shown in FIG. 4, foot plate 48 is connected to first telescoping bracket 38 of foot bracket 36 via pin 70 and flexible grommet 72. Foot plate 48 is also connected to first telescoping bracket 44 of foot bracket 42 via a second pin and a second flexible grommet identical to that of pin 70 and flexible grommet 72.

As shown in FIG. 4, because of flexible grommet 72, foot plate 48 is capable of pivoting up and down about pin 70 within arc C. Likewise, foot plate 48 can pivot about the second pin connecting foot plate 48 to first telescoping bracket 44 of foot bracket 42 about a pivot pin within a similar arc. This design permits a "twisting" of splint 10 such that foot bracket 36 can pivot within arc A and foot bracket 42 can pivot without arc B, independent of each other.

The design shown in FIGS. 1–4 permit range-of-motion splint 10 to accommodate foot inversion, which is the twisting of the foot from left to right or right to left during flexion or extension of the ankle joint. Flexible grommet 72 and the flexible grommet which connects foot plate 48 to first telescoping bracket 44 of foot bracket 42 permits the angle between first telescoping bracket 38 of foot bracket 36 and foot plate 48 and the angle between first telescoping bracket 44 of foot bracket 42 and foot plate 48 to vary. If foot plate 48 was securely connected to foot brackets 36 and 42, the angles between foot plate 48 and foot brackets 36 and 42 would remain constant. This type of design would not accommodate foot inversion, and the rehabilitation process would be limited, as well as uncomfortable for the patient.

Pivot assembly 74, shown in FIGS. 5–9, includes ankle bracket 18, foot bracket 36 and an elongated link 75 pivotally connected at one end to ankle bracket 18 by pivot pin 98. An identical pivot assembly would be provided between ankle bracket 24 and foot bracket 42. Pivot pin 98 defines a first or primary joint pivot axis about which ankle bracket 18 and foot bracket 36 rotate. The end of bracket 36 interconnects with pivot assembly 74 and includes elongated gap 76 forming extensions 77 on opposite sides of the bracket. The ends of extensions 77 are pivotally connected to the sides of link 75 by screws 78. Screws 78 define a second or lateral joint pivot axis which is perpendicular to the primary splint pivot axis. Gap 76 is sized to receive link 75 while allowing foot bracket 36 to pivot with respect to ankle bracket 18 about the lateral joint pivot axis. Ankle bracket 18 includes extension 79 which extends beyond pivot pin 98 toward foot bracket 36 and is configured to engage pivot pin 94 of locking mechanism 120 (described below) to limit the range of rotational motion of ankle bracket 18 and foot bracket 36.

Drive assembly 80, which is housed in housings 54 and 60, is now described with reference to FIGS. 5–9. While drive assembly 80 is shown and described with reference to ankle bracket 18, foot bracket 36, and housing 54, it is understood that an identical drive assembly would be housed within housing 60. Drive assembly 80 includes drive mechanism 82, spiral spring 84 having inner end 86 and outer end 88, gear 90 having shaft 92, pivot pin 94, link 96, pivot pin 98, gear pivot pin 100, recess 102 of housing 54, and screws 104.

As shown in FIGS. 5–9, drive assembly 80 includes drive mechanism 82 mounted to ankle bracket 18 and foot bracket 36 and enclosed by housing 54. Drive mechanism 80 includes spiral spring 84 having first or inner end 86 and second or outer end 88. Inner end 86 is mounted to a slot within shaft 92 of gear 90. Outer end 88 is hooked to pivot pin 94 extending from the end of link 96 opposite pivot pin 98. Gear 90 is rotatably mounted within housing 54 by gear pivot pin 100 which extends through gear shaft 92. The end of gear pivot pin 100 adjacent gear 90 is mounted within recess 102 on the inner surface of housing 54. The end of gear pivot pin 100 adjacent shaft 92 is rotatably mounted within a recess or aperture in ankle bracket 18. Housing 54 is fastened to ankle bracket 18 by screws 104.

Spiral spring 84 is eccentrically mounted with respect to the primary splint pivot axis formed by pivot pin 98. As shown in FIGS. 6–9, the rotational axis of gear pivot pin 100 is offset or spaced from pivot pin 98. In the embodiment shown, when ankle bracket 18 and foot bracket 36 are linearly aligned, a line (not shown) extending through pins 98 and 100 form a 90 degree angle with a line (also not shown) extending through pins 94 and 98. In other words, pins 94 and 100 form a right angle with respect to pivot pin 98. The offset between gear pivot pin 100 and pin 98 is ¼ inch (64 mm) in one embodiment.

Figure 9:
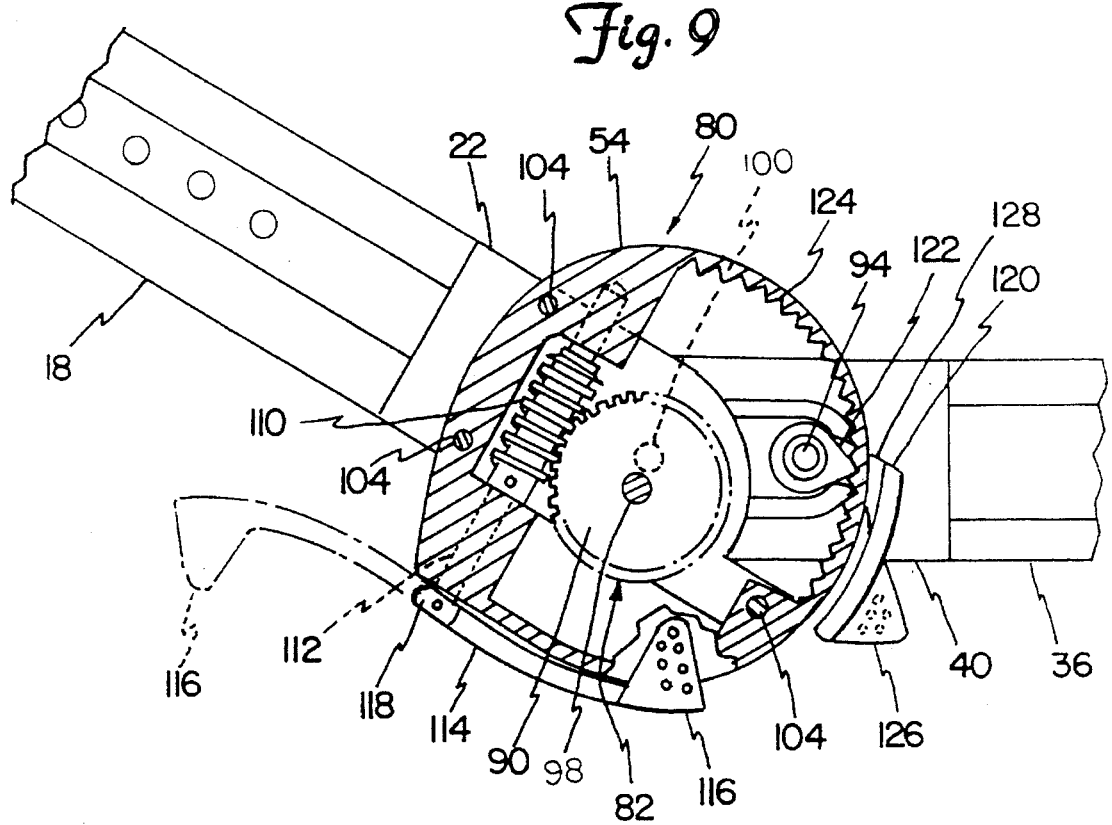
FIG. 9 is a detailed end view of the drive assembly as shown from line 9—9 of FIG. 5, illustrating the torque adjustment mechanism.

As shown in FIGS. 5 and 9, a torque adjustment mechanism is shown which includes adjustment worm 110 having end 112, crank 114 having handle 116, and pivot 118.

As shown in FIGS. 5 and 9, adjustment worm 110 is mounted with recesses in housing 54 for engagement with gear 90 and rotation about an axis perpendicular to gear pivot pin 100. End 112 of adjustment worm 110 extends through housing 54 and is connected to crank 114 by pivot pin 118. Crank 114 is configured for pivotal movement about a retracted position adjacent housing 54 (shown in solid lines), and an extended position (shown in broken lines). When in the extended position, handle 116 of crank 114 can be actuated to rotate adjustment worm 110, thereby rotating gear 90 to wind and unwind spiral spring 84 in order to increase and decrease the amount of torque applied across ankle bracket 18 and foot bracket 36 by spring 84. Gear 90, adjustment worm 110 and crank 114 thereby function as a torque adjustment mechanism.

Figure 8:
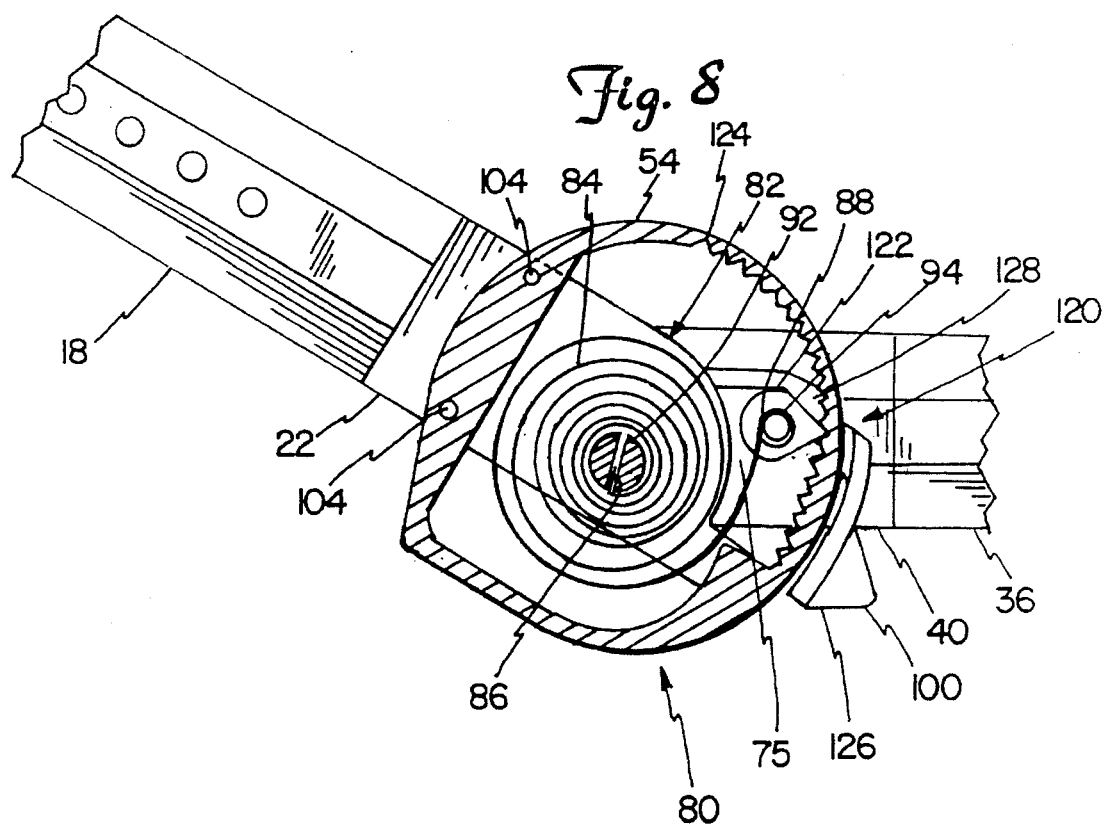
FIG. 8 is a detailed end view of the drive assembly as shown from line 8—8 of FIG. 5, illustrating the spring and lock mechanism.

FIGS. 8 and 9 show locking mechanism 120 which can releasably lock ankle bracket 18 and foot bracket 36 with respect to one another. Locking mechanism 120 includes pawl 122, rack 124, lever 126 and base member 128 having handle 130. Locking mechanism 120 includes pawl 122 pivotally mounted to pivot pin 94 and rack 124 formed on interior surface of housing 54. Pawl 122 is actuated by lever 126 which includes base member 128 and handle 130. Base member 128 is mounted to pawl 122 and extends outwardly from housing 54. Handle 130 extends from base member 128 and is positioned generally adjacent to the exterior of housing 54. Handle 130 is actuated to drive pawl 122 between a position disengaged from rack 124, and an over-center position engaged with rack 124. When pawl 122 is in the disengaged position, ankle bracket 18 and foot bracket 36 can freely rotate with respect to one another. Conversely, when pawl 122 is in the engaged position, pawl 122 is biased into engagement with rack 124 by the force of spiral spring 84.

Locking mechanism 120 enables ankle bracket 18 and foot bracket 36 to be conveniently and rigidly locked with respect to one another at any desired position within the range-of-motion of splint 10. In one embodiment, the teeth forming rack 124 are symmetrical or bi-directional. Housing 54 can therefore be used on range-of-motion splint 10 configured for both flexion and extension contractures of an ankle joint.

Figure 6:
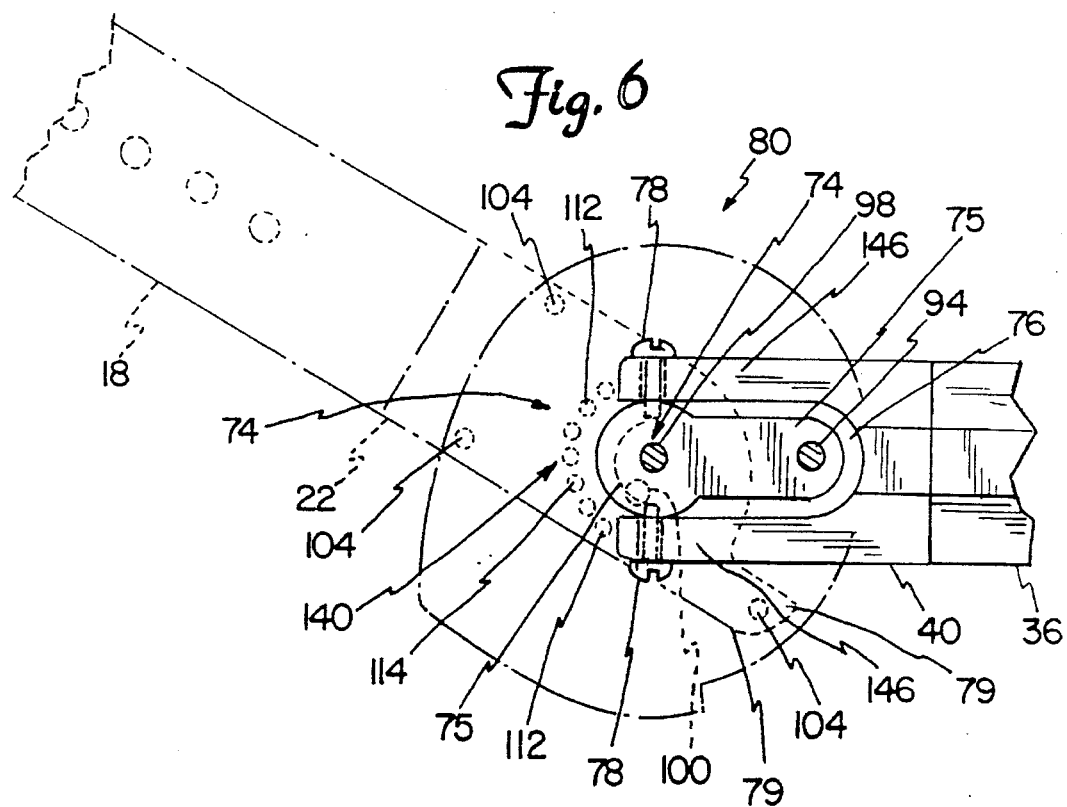
FIG. 6 is a detailed end view of the drive assembly as shown from line 6—6 of FIG. 5, illustrating the pivot assembly.
Figure 7:
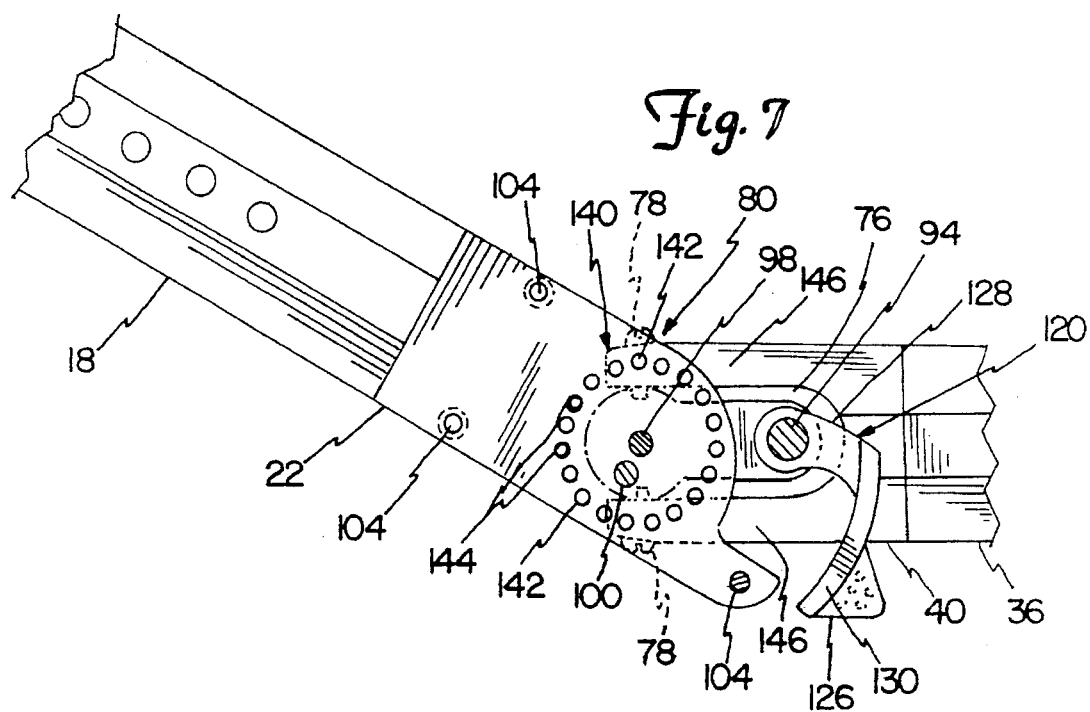
FIG. 7 is a detailed end view of the drive assembly as shown from line 7—7 of FIG. 5, illustrating the pivot assembly.

Adjustable range-of-motion stop mechanism 140 is shown in FIGS. 5–7. Adjustable range-of-motion stop mechanism 140 includes threaded holes 142 and pins 144. Adjustable range-of-motion stop mechanism 140 enables a clinician to control the range of rotational motion between ankle bracket 18 and foot bracket 36. Stop mechanism 140 includes threaded holes 142 circumferentially arranged around pivot pin 98 on the end of ankle bracket 18 and a pair of removable pins 144 which can be threadably engaged with holes 142. Pins 144 extend from the side of ankle bracket 18 facing foot bracket 36. The range of rotational motion between ankle bracket 18 and foot bracket 36 is limited by the engagement of pins 144 with the ends of extensions 146 of foot bracket 36. A clinician can conveniently reposition one or both of pins 144 within holes 142 to adjust the range-of-motion over which splint 10 can operate as the patient's condition improves.

FIG. 10 is a side view of an alternate embodiment of the present invention. As shown in FIG. 10, several elements are identical to that disclosed in the embodiment shown in FIGS. 1–9. Thus, any like elements have been labeled as such.

As shown in FIG. 10, ankle hook 30, ankle pad 32 and ankle strap 34 have been removed. In their place is front ankle pad 100, outside ankle pad 102, front ankle strap 104, back ankle strap 106 and heel strap 108. The embodiment shown FIG. 10 provides a secure fit to the lower leg of a patient, while also providing comfort to the patient.

FIG. 11 is an exploded view of a portion of the alternate embodiment shown in FIG. 10, while FIG. 12 is a side view of the present embodiment with housing 54 removed for clarity. As shown in FIGS. 11 and 12, pin 110 can be positioned through plate 112 and fasteners 114, 116 and 118. Fasteners 114, 116 and 118 are connected to the ends of straps 104, 106 and 108 respectively. This type of connection allows straps 104, 106 and 108 to pivot about pin 110 in order to provide maximum comfort and stability. It is understood that there is an identical arrangement on the inside of the patient's foot. This view has not been shown to avoid duplicate drawings.

Range-of-motion splint 10 offers considerable advantages over prior art mechanisms. First, the use of two torque adjustment mechanisms provide for individual biasing on either side of an ankle joint. Second, the use of flexible grommets connecting the foot plate to the two foot brackets accommodates foot inversion, which is the twisting of the foot during flexion contractures of the ankle joint. Third, the flexibility of having either an ankle bracket or three straps provides maximum comfort and stability.

Although the present invention has been described with reference to preferred embodiments, workers skilled in the art will recognize that changes may be made in form and detail without departing from the spirit and scope of the invention.

What is claimed is:

1. A range-of-motion splint for applying torque to an ankle joint of a patient, the splint comprising:

a foot plate for supporting a foot of the patient;

a first foot bracket connected to the foot plate;

a second foot bracket connected to the foot plate;

a first ankle bracket;

a second ankle bracket;

first pivot means for pivotally connecting the first foot bracket to the first ankle bracket;

second pivot means for pivotally connecting the second foot bracket to the second ankle bracket;

foot securing means connected to the foot plate for securing the foot of the patient to the foot plate;

calf securing means connected to the first and second ankle brackets for securing the first and second ankle brackets to a calf of the patient;

a front ankle strap pivotally connected to the first and second pivot means for adjustably positioning above the foot in front of the ankle joint;

a back ankle strap pivotally connected to the first and second pivot means for adjustably positioning behind the ankle joint; and a heel strap pivotally connected to the first and second pivot means for adjustably positioning beneath the ankle joint.

2. The splint of claim 1 wherein the foot securing means further comprises:

a pad of flexible material.

3. The splint of claim 1 and further comprising:

an ankle hook connected to the first and second ankle brackets; and a calf hook connected to the first and second ankle brackets.

4. The splint of claim 3 wherein the calf securing means secures the calf hook to the calf of the patient.

5. The splint of claim 1 wherein the first torque applying means further comprises:

a first spring-engaged mount on the first ankle bracket at a position spaced from the first pivot means;

a second spring-engaged mount on the first foot bracket at a position spaced from the first pivot means; and a first spiral spring having an inner end and an outer end for applying torque between the first foot bracket and the first ankle bracket, the inner end mounted to the first spring-engaged mount and the outer end mounted to the second spring-engaged mount.

6. The splint of claim 5 and further comprising:

a first torque adjustment mechanism for adjusting the torque applied by the first spiral spring between the first foot bracket and the first ankle bracket.

7. The splint of claim 6 wherein the first torque adjustment mechanism further comprises:

a first gear rotatably connected to the first ankle bracket at the position of the first spring-engaged mount, such that the inner end of the spring is connected to the gear; and a first adjustment worm rotatably connected to the first ankle bracket and engaged with the first gear for rotating the first gear to adjust the tension of the first spiral spring.

8. The splint of claim 7 and further comprising:

a first cover connected to the first ankle bracket for enclosing the first spiral spring and first torque adjustment mechanism; and a first handle connected to the first adjustment worm and capable of movement between a retracted position adjacent the first cover and an extended position, such that the first handle can rotate the first adjustment worm when in the extended position.

9. The splint of claim 8 and further comprising:

a first locking mechanism connected to the first foot bracket for releasably engaging the first cover and locking the angular position of the first ankle bracket with respect to the first foot bracket.

10. The splint of claim 9 and further including a second torque adjustment mechanism for adjusting the torque applied by the second spiral spring between the second foot bracket and the second ankle bracket.

11. The splint of claim 10 wherein the second torque adjustment mechanism further comprises:

a second gear rotatably connected to the second ankle bracket at the position of the second spring-engaging mount, such that the inner end of the second spring is connected to the second gear; and a second adjustment worm rotatably connected to the second ankle bracket and engaged with the second gear for rotating the second gear to adjust the tension of the second spiral spring.

12. The splint of claim 11 and further comprising:

a second cover connected to the second ankle bracket for enclosing the second spiral spring and second torque adjustment mechanism; and a second handle connected to the second adjustment worm and capable of movement between a retracted position adjacent the cover and an extended position, such that the handle can rotate the second adjustment worm when in the extended position.

13. The splint of claim 12 and further comprising:

a second locking mechanism connected to the second foot bracket for releasably engaging the second cover and locking the angular position of the second ankle bracket with respect to the second foot bracket.

14. The splint of claim 1 wherein the first pivot means is positioned at a primary axis of the ankle joint.

15. The splint of claim 14 and further comprising:

third pivot means for pivotally connecting the first ankle bracket and the first foot bracket for motion about a third pivot axis corresponding to a secondary axis of joint motion between the first ankle bracket and the first foot bracket.

16. The splint of claim 15 wherein the third pivot means includes a mechanism for pivotally connecting the first ankle bracket and the first foot bracket for rotation about the third pivot axis which is perpendicular to the first pivot axis.

17. The splint of claim 15 wherein the third pivot means includes a mechanism for pivotally connecting the first ankle bracket and the first foot bracket for rotation about the third pivot axis which intersects the first pivot axis.

18. The splint of claim 15 wherein the second pivot means is positioned at a primary axis of the ankle joint.

19. The splint of claim 18 and further comprising:

fourth pivot means for pivotally connecting the second ankle bracket and the second foot bracket for rotation about a fourth pivot axis corresponding to a secondary axis of joint motion between the second ankle bracket and the second foot bracket.

20. The splint of claim 19 wherein the fourth pivot means includes a mechanism for pivotally connecting the second ankle bracket and the second foot bracket for rotation about the fourth pivot axis which is perpendicular to the second pivot axis.

21. The splint of claim 19 wherein the fourth pivot means includes a mechanism for pivotally connecting the second ankle bracket and the second foot bracket for rotation about the fourth pivot axis which intersects the second pivot axis.

\* \* \* \* \*